United States Patent [19]

Besemer et al.

[11] Patent Number: 5,104,813

[45] Date of Patent: Apr. 14, 1992

[54] DILUTION AND MIXING CARTRIDGE

[75] Inventors: Don Besemer, Los Altos Hills; Michael Gorin, Palo Alto; Ian Gibbons, Menlo Park, all of Calif.

[73] Assignee: Biotrack, Inc., Mountain View, Calif.

[21] Appl. No.: 337,286

[22] Filed: Apr. 13, 1989

[51] Int. Cl.5 .................... G01N 21/00; G01N 1/10
[52] U.S. Cl. .................... 436/179; 436/180; 436/165; 422/100; 422/58; 422/102; 422/82.05; 422/106; 422/105
[58] Field of Search .............. 356/246; 422/50, 58, 422/61, 100, 102, 82.05, 106, 105; 436/165, 174, 180, 179

[56] References Cited

U.S. PATENT DOCUMENTS

| 4,868,129 | 9/1989 | Gibbons et al. | 422/100 |
| 4,876,203 | 10/1989 | Guigan | 436/179 |
| 4,883,763 | 11/1989 | Holen et al. | 422/102 |
| 4,985,204 | 1/1991 | Klose et al. | 436/165 |
| 4,999,304 | 3/1991 | Robertson | 436/179 |

FOREIGN PATENT DOCUMENTS 212314 4/1987 European Pat. Off.
305210 1/1989 European Pat. Off. ............ 422/100

Primary Examiner—Robert J. Warden
Assistant Examiner—Theresa A. Trembley
Attorney, Agent, or Firm—Cooley, Godward Castro Huddleson & Tatum

[57] ABSTRACT

A dilution and mixing cartridge is provided that allows single (or multiple) dilutions of a sample with a diluent in a disposable cartridge in which a measurement, such as optical density, is made. Addition of sample to the device automatically measures the sample, and addition of diluent automatically causes a fixed ratio of sample and diluent to enter a receiving chamber, in which mixing and measurement can take place. A number of preferred embodiments are provided in which the diluent application site is located at a vertical height below the sample application site, flow directing chambers are provided to control flow of desired volumes of sample or diluted sample at the appropriate locations in the device and to direct excess sample and diluent to waste locations, or control mechanism are provided at flow directing chambers and other internal locations to verify correct operation of the device.

44 Claims, 3 Drawing Sheets

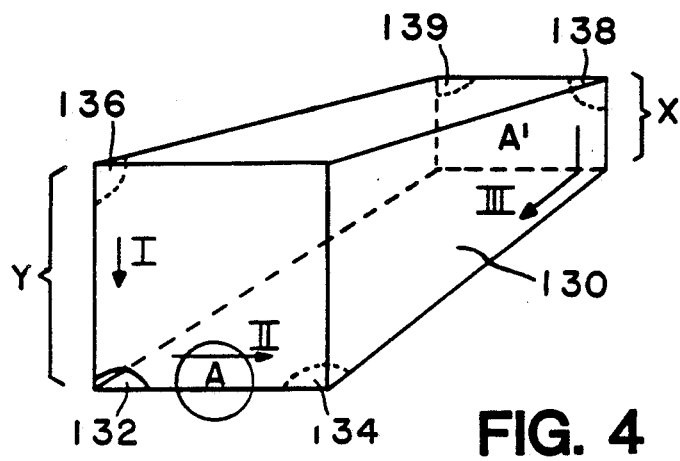
FIG. 4
FIG. 5
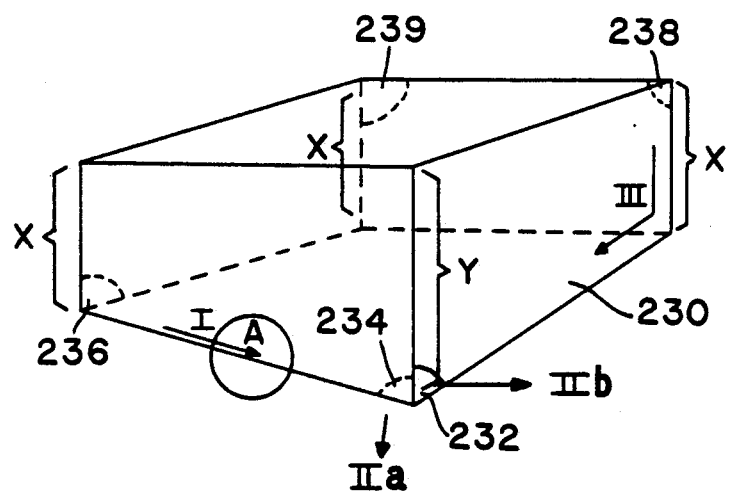

DILUTION AND MIXING CARTRIDGE

TECHNICAL FIELD

This invention relates to methods and apparatuses used for diluting and mixing liquids, particularly the automatic measuring and diluting of small volumes of liquids.

BACKGROUNDS

There has been a recent period of explosive growth in the field of clinical analysis intended to be carried out by unskilled users. Numerous approaches have been developed which allow an unskilled user, such as a diabetic patient, to determine the presence and/or amount of an analyte in a sample, such as glucose in urine. The devices that carry out such analyses are generally intended to be "user friendly" in that they require little training and are essentially fool-proof in use. Typical of these devices are the so-called "dipsticks". These devices are plastic strips with a reagent-containing matrix layered thereon. Sample is applied to the strip, and the presence or absence of an analyte is indicated by a color-forming reaction.

While such devices have proven useful for the qualitative determination of numerous substances in biological samples, not all analyses can be carried out in this manner. For example, some techniques require dilution and/or mixing of small quantities of sample. Measurement of extremely small amounts (E.G., microliter amounts) of liquid and the dilution thereof typically require significant training or the use of expensive equipment to carry out the dilution. Neither of these alternatives is convenient or easy to carry out.

Measuring and dilution of small samples of liquid is readily carried out in a number of automatic analyzers. However, these are not suitable for use in the home or in a doctor's office because of their size and expense. For example many devices are available in which a sample of liquid is drawn into a conduit which is in the form of a capillary tube that acts as a metering device. However, this metering device is part of a large apparatus containing pistons and numerous other moving parts, such as vacuum pumps, that are required for movement of the sample and diluent. The precision with which such moving parts must be manufactured in order to retain liquid-tight seals significantly increase the cost of the device.

As an alternative to large automatic analyzers, small hand-held micropipets, such as the well known Eppendorf® pipet, have been devised. These pipets utilize a precision piston to draw sample or diluent into a small disposable tip. However, skill is required in the use of the pipet, and a number of precise manual operations must be carried out to successfully measure sample and diluent. Skill is also required in mixing the resulting small-volume solution.

Another technique that has been developed for the home uses a capillary tube to measure a sample of fluid. The entire capillary tube is then placed into a large container which holds a measured quantity of diluent or to which a measured quantity of diluent is added. However, such devices are not generally satisfactory in the hands of an unskilled user, since capillary tubes are easily broken and since contamination of the outside of the capillary results in volume error.

Accordingly, there is a need for simple and accurate methods and devices for measuring, diluting, mixing, and analyzing small quantities of sample.

Relevant Literature

West German published patent application DE3328964C1, publication date Feb. 14, 1985, describes a device for the automatic, discontinuous sampling of fluids using a capillary tube that acts as a measuring device and which can be either dipped into a fluid being sampled or alternatively moved into a position from which the sample is transported with a diluent to an analyzer by a pump or suction. U.S. Pat. No. 4,454,235 describes a capillary tube holder for liquid transfer in immunoassays. U.S. Pat. No. 4,233,029 describes a liquid transport device formed by opposed surfaces spaced apart a distance effective to provide capillary flow of liquid without providing any means to control the rate of capillary flow. U.S. Pat. Nos. 4,618,476 and 4,233,029 describe a similar capillary transport device having speed and meniscus control means. U.S. Pat. No. 4,426,451 describes another similar capillary transport device including means for stopping flow between two zones, flow being resumed by the application of an externally-generated pressure. U.S. Pat. Nos. 3,811,326; 3,992,150; 4,537,747; and 4,596,780 describe various processes and devices in which a capillary tube is used to take up a predetermined volume of the test solution and the charged capillary is then placed in a cuvette or other container of liquid that is used as reagent or diluent. U.S. Pat. No. 3,799,742 describes an apparatus in which a change in surface character from hydrophilic to hydrophobic is used to stop flow of a small sample, thereby metering the sample present. U.S. application Ser. No. 117,791, filed Nov. 5, 1987, and U.S. Pat. No. 4,868,129 1987, both of which are assigned to the same assignee as the present application, described a number of dilution and mixing cartridges.

SUMMARY OF THE INVENTION

The present invention provides an improved self-contained dilution apparatus that does not require the use of externally generated force (except gravity) to move liquids between its various parts and provide for reproducible dilution of samples. The apparatus can provide for a single dilution or for serial dilutions; i.e., dilution of a sample with a first diluent followed by dilution of the mixture with the same, a second, or a further diluent. When prepared in the form of a disposable cartridge, the cartridge housing contains sample receiving means for receiving a liquid sample, a flow directing chamber comprising an internal chamber in the housing, sample flow means for delivering sample from the sample receiving to the flow directing chamber, diluent receiving means for receiving a liquid diluent, diluent flow means for delivering diluent from the diluent receiving means to the flow directing chamber, a receiving chamber comprising a vented internal chamber in the housing having a first volume, a measuring chamber comprising a vented internal chamber in the housing having a second volume smaller than the first volume, the measuring chamber connecting the flow directing chamber to the receiving chamber and being capable of delivering sample and diluent from the flow directing chamber to the receiving chambers solely by capillary and gravitational forces, a stop flow junction located at the intersection of the measuring chamber and the receiving chamber, wherein the stop flow junction is adapted to the surface tension characteristics of the sample so as to provide sufficient back pressure resulting from contact between the sample and walls of the housing at the stop junction to prevent the sample from flowing through the stop flow junction in the absence of diluent but allowing flow through the stop flow junction when the diluent receiving means receive diluent and diluent enters the flow directing chamber, waste means for emptying the flow directing chamber after sample has entered the flow directing chamber and the sample has filled the measuring chamber, wherein the waste means operates by capillary and gravitational forces, whereby diluent added to the diluent receiving means after sample has been added to the sample receiving means flow through the flow control member and expels sample from the measuring chamber into the receiving chamber, thereby causing a fixed ratio of sample to diluent to be delivered to the receiving chamber.

In some embodiments, a second dilution of the initial mixture is provided by using a valve to control passage of liquid from the mixing chamber to a hydrostatically connected mixture isolating chamber. In preferred embodiments, the mixture isolating chamber is similar to the first series of chambers and flow means as described above, although other arrangements are also possible.

A number of particularly useful embodiments are described that avoid a number of minor problems associated with previous dilution and mixing cartridges.

BRIEF DESCRIPTION OF THE DRAWINGS

The present invention will be better understood by reference to the following detailed description of the invention when considered in conjunction with the attached drawings that form a part of the present specification, wherein:

FIG. 4 is an expanded perspective view of a first flow directing chamber of the invention.

FIG. 5 is an expanded perspective view of a second flow directing chamber of the invention.

DESCRIPTION OF SPECIFIC EMBODIMENTS

Figure 1:
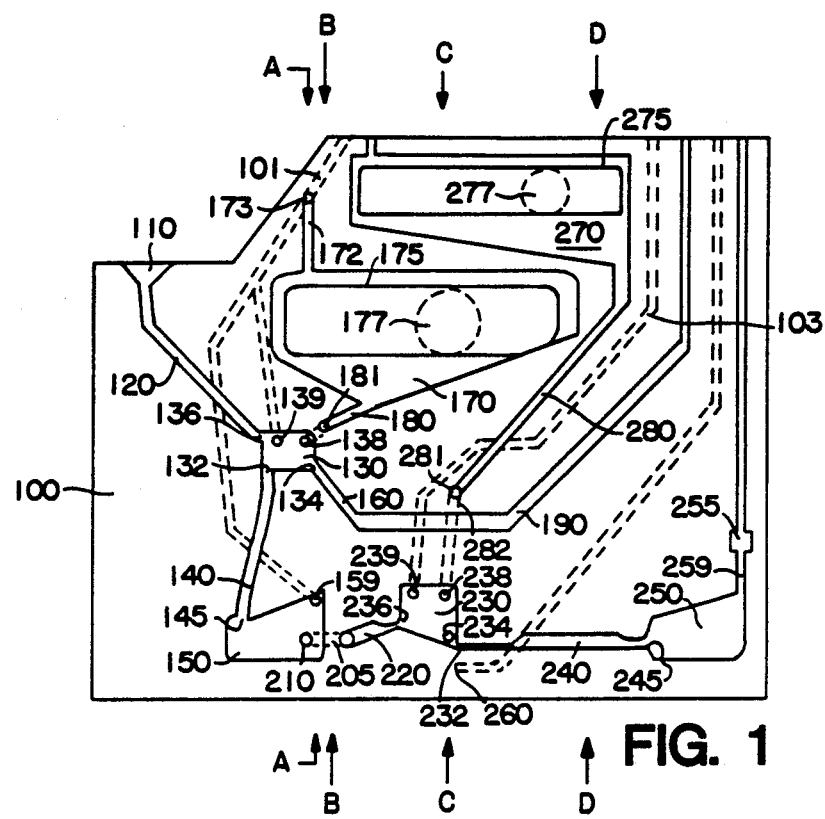
FIGS. 1 is a vertical cross-sections of a first embodiment of the invention.

The present invention provides an apparatus and a method by which small samples can easily be measured and diluted. The apparatus is small, convenient to use, and requires no moving parts for the movement of fluid, gravity and capillary action being sufficient to provide all fluid motive forces required for the sample measurement and dilution steps. The apparatus of the present invention resembles dilution and mixing cartridges described in U.S. application Ser. No. 117,791, filed Nov. 5, 1987, and U.S. Pat. No. 4,868,129. However, the apparatuses of the present invention provide a number of improvements over the previously provided dilution and mixing apparatuses; particularly in ease and security of operation. Among the specific improvements of the present apparatus are flow directing chambers that provide flow of desired volumes of samples (or diluted sample) at appropriate locations in the apparatus to a measuring chamber while directing excess sample to waste locations, provisions to allow the dilution application site to be located at a vertical height below the sample application site, and various control devices provided in the monitor into which the cartridge is inserted to verify correct operation of the device.

As with the apparatuses described in U.S. application Ser. No. 090,026 and 117,791, the cartridge of the present invention includes a sample application site, a diluent application site, a measuring chamber, a mixing (receiving) chamber, various channels to provide flow of liquid between parts, and, in the case of serial dilutors, a mixture isolating and measuring chamber and at least one valve controlling passage of fluid from the mixing chamber to the mixture isolating and measuring chamber. All of these parts of the cartridge have been described in the indicated applications, which can be referred to for greater detail if desired.

One of the key aspects of the present device is a flow directing chamber, a non-capillary internal chamber which receives both sample and diluent and directs a portion of the sample into a measuring chamber while directly the remainder of the sample into a waste chamber. When diluent reaches the flow directing chamber, sample contained in the measuring chamber is expelled into the receiving chamber, which then fills with a defined ratio of sample and diluent. The flow directing chamber also allows monitoring of proper operation of the dilutor to an extent not previously possible.

The apparatus of the invention can provide for a single dilution, as in the valveless dilutors described in U.S. Pat. No. 4,868,129. Serial dilutions can be provided for using a valve to control passage of a portion of the initially obtained mixture into a mixture isolating and measuring chamber. This mixture isolating chamber can take any of the forms described in U.S. application Ser. No. 117,791. However, in preferred embodiments as described herein, the mixture isolating chamber contains essentially the same chambers and passageways as the initial diluting pathway described above. All of these parts are described in greater detail below. The following detailed description of the various parts of the apparatus is organized by following the course of action as a sample is applied to the apparatus and is diluted.

The sample is a liquid and may be derived from any source, such as a physiological fluid; E.G., blood, saliva, ocular lens fluid, cerebral spinal fluid, pus, sweat, exudate, urine, milk, or the like. The liquid sample may be subjected to prior treatment, such as preparing serum or plasma from blood or dissolving or suspending a solid in a liquid. Examples of sample treatments prior to application to the apparatus of the invention include concentration, filtration, distillation, dialysis, inactivation of natural components, chromatography, and addition of reagents. In addition to physiological fluids, other liquid samples can be employed. Examples of other liquid samples include process streams, water, plant fluids, chemical reaction media, biological growth media, and the like. For the most part, the liquid will be aqueous, although other liquids can be employed. Aqueous media may contain additional miscible liquids, particularly oxygenated organic solvents, such as lower alkanols, dimethyl formamide, dimethyl sulfoxide, acetone, and the like. Usually the solvents will be present in less than about 40 vol %, more usually in less than about 20 vol %, in order to maintain the high surface tension that is present in aqueous solutions. However, the apparatus of the invention can be modified as described below for use with liquids exhibiting different surface tensions.

The sample application site (also referred to as a sample receiving site) will generally be a cavity on a surface of the apparatus or may simply be an opening (optionally surrounded by a ring or tube) leading to the interior of the apparatus. The sample application site can contain a filter, for example, to separate red blood cells from plasma (see U.S. Pat. No. 4,753,776), or may represent a connection between the apparatus of the invention and some other apparatus that manipulates the sample prior to its entering the present dilution apparatus. For example, the application site can be a recess into which a standard capillary tube will fit.

When the sample application site is a recess for insertion of a capillary tube, the capillary tube can act either as a convenient means for transferring the sample or can act as a measuring chamber, either by completely filling the capillary or by filling the capillary to a particular mark. The sample application site in such embodiments acts as a point of transfer.

In other cases, the sample application site will be an external chamber, such as a recess on an upper surface of the device into which sample is inserted. Such surface recesses are referred to herein as external chambers, to distinguish them from chambers located in the interior of the housing that forms the cartridge. The application site can be provided with a raised lip surrounded by a catch basin so that the application site can be filled to overflowing, with excess sample overflowing into the catch basin. Means for draining off a large excess of sample or sample inadvertently applied to the wrong location are discussed in U.S. Pat. No. 4,868,129 and U.S. application Ser. No. 117,791, discussed above.

When sample is applied to the sample application site, the liquid sample normally flows without the application of external force (except unassisted gravity) through a fluid passageway into a flow directing chamber, comprising an internal chamber in the housing that forms the apparatus. External force, E.G., from compressed air, can be used to move the sample to the flow directing chamber but is not required and in fact is not preferred. The flow directing chamber acts to divert a portion of the sample that first enters the flow directing chamber into a sample measuring chamber, which has a predetermined volume and which operates to measure and hold a portion of the sample for dilution. The remainder of the sample that enters the flow directing chamber is automatically diverted by the flow directing chamber into an exit port leading to a waste chamber or to some other means of disposing of excess sample beyond that required to fill the sample measuring chamber.

The flow directing chamber is essentially a small, non-capillary, internal chamber in the apparatus having entrances and exits for sample and diluent. By "non-capillary" is meant that flow of liquid through the chamber requires gravitational assistance. In preferred embodiments, one exit is the opening connecting the measuring chamber to the flow directing chamber. The other exit provides a flow connection with the waste chamber. The entrances for sample and diluent are generally connections to capillary pathways leading to the sample application site and the diluent application site. The exits are located at gravitationally low points in the flow directing chamber with the entrances being located above the exits so that liquid flows from the entrances to the exits under the influence of gravity.

The entrances and exits are located to insure that the measuring chamber is filled with the available sample. Such filling can take place by locating the sample entrance so that sample reaches the entrance to the measuring chamber before sample reaches the entrance to the waste chamber. For example, by locating the entrance for sample flow above the measuring chamber exit and closer to the measuring chamber exit than to the waste flow exit, sample initially entering the flow directing chamber can be directed to the measuring chamber. When the measuring chamber fills, as discussed below, excess sample flows past the measuring chamber entrance to the waste chamber entrance. By providing appropriate geometry of a flow directing chamber and the waste exit (or other provision for removing waste sample), all excess sample will be drained out of the flow directing chamber so that when diluent later enters the flow directing chamber, only sample in the measuring chamber will be expelled into the receiving chamber as described below.

Since diluent entering the flow directing chamber will mix with any sample remaining in this chamber and be divided unpredictably between the receiving chamber and waste means, it is desirable to reduce the amount of sample left in the flow directing means as much as possible. The amount of sample left in the flow directing chamber will be less than the maximum allowed by the accuracy of the test being employed. For example, if the test is accurate to 10%, the volume of sample left in the flow directing chamber will be less than 10% of the volume of sample captured in the sample measuring chamber. Preferably, this amount is less than 5%, more preferably less than 2%, even more preferably less than 1% of the measured sample volume.

A number of different geometries can be provided to achieve the desired result. For example, the flow directing chamber can be essentially in the shape of a truncated cube or wedge so as to provide a horizontal surface and vertical sides with a floor sloping downward in the direction of one axis (the axes being defined by the walls that intersect at right angles). This is essentially the shape of the first control chamber shown in the apparatus of FIG. 1, which is discussed below in more detail. The sample measuring chamber exit and waste exits are located at the two bottom corners of the chamber, which are located at equal heights (in a gravitational field). The sample enters the waste chamber at the corner directly above the sample measuring chamber, and diluent enters the chamber near the corner diagonally opposite the corner of the upper surface where the sample enters.

Alternatively, the flow directing chamber can be essentially a truncated cube as described above but with a floor sloping downward along two axis (i.e., diagonally) to provide a single low point at one corner of the "cube." This is essentially the shape of the second flow directing chamber of the apparatus of FIG. 1. In the first type of chamber discussed above, the sample measuring exit and waste exit are spaced apart. In this second embodiment, they are located close together at the single low point in the chamber. In both cases, however, the waste exit is located at a gravitational low point in the chamber to ensure that all of the sample that is to be diluted that enters the chamber is removed from the chamber before diluent reaches the chamber. When the two chamber exits are located close together so that sample reaches them at essentially the same time, the sizes of the exits can be adjusted to insure that sample fills the measuring chamber before sample is depleted.

Other geometries are also possible. For example, it is possible to have sample reach the waste exit before reaching the sample measuring exit if the exits are properly sized to insure that sufficient sample reaches the measuring chamber before sample in depleted by the waste exit. Likewise, the waste exit need not be at the absolute lowest gravitational point in the chamber if other means are provided to insure that all excess sample is drained from the flow directing chamber. For example, edge effects resulting from surface tension of the sample can be used to draw excess sample along an edge of a chamber from a low point in the chamber to a somewhat higher exit. It is also possible to use flow deflectors, usually projections or grooves in the walls of the flow directing chamber, to direct flow to the correct locations.

It is preferred to have the initial portion of the waste exit be of capillary dimensions to assist in drawing excess sample out of the flow directing chamber. It is also possible to use a porous material to "wick" excess sample from the flow directing chamber, as this is also a capillary action resulting from surface effects in the fine pores of the porous material. Example of porous materials include cotton, paper, cellulose fibers, glass fiber pads, and porous ceramics. The porous materials are used in the form of a wicking element that can contact the excess sample at an appropriate location in the flow directing chamber or that are present in waste chambers connected to the flow directing chamber by a capillary. Techniques for wicking excess sample from the sample application site into a waste chamber are described in U.S. Pat. application No. 117,791, described above, and can be adapted for use in the present invention to wick excess sample from the flow directing chamber. Those skilled in the art will be able to adjust the geometry of the chamber and to provide absorbent materials (when used) as necessary, using the guidance provided herein, to achieve the desired result of filling the measuring chamber with sample and draining the flow directing chamber of excess sample before diluent is added.

The measuring chamber can be a capillary channel or chamber, in which case capillary action will aid or in some cases provide all the force necessary for filling the measuring chamber with sample from the sample application site by way of the flow directing chamber. Capillary channels and chambers will generally have at least one dimension perpendicular to the flowpath in the range 0.01 to 2.0 mm, more generally 0.1 to 1.0 mm. Capillary spaces (of whatever type) have at least one dimension at right angles to the direction of flow in the range required to support flow. Capillary channels have both dimensions at right angles to the direction of flow in the range required to support flow. Capillary chambers have one dimension at right angles to flow that would not support capillary flow but provide for capillary flow by having the second dimension at right angles to flow in the required range (similar to the space between two flat plates that are closely spaced). However, larger measuring chambers that are not capillary in any dimension are also possible. The sample measuring site is said to be in "fluid receiving relationship" to the flow directing chamber in order to indicate that unassisted flow occurs. In order for proper operation of the stop flow junction to occur, it is essential that the measuring chamber be filed solely by capillary and gravitational forces, as will be apparent from the description of the stop flow junction below.

The geometry of the measuring chamber is such that when diluent is added to the apparatus at a later step, essentially all of the sample in the measuring chamber will be expelled into the receiving chamber. One means of accomplishing this is by providing for smooth flow of diluent through the measuring chamber. A straight or curved tube with an essentially constant cross section open at both ends is thus a preferred embodiment for this type of measuring chamber. This type of measuring chamber is seen in the first measuring chamber (140) of FIG. 1. In preferred embodiments of this type, diluent enters the measuring chamber in a front across the entire cross-sectional area of flow. This helps avoid mixing of diluent with sample and passage of diluent through the measuring chamber without expelling essentially all of the sample, which can occur if a small stream of diluent enters into a broader cross-sectional area of the measuring chamber.

However, measuring chambers that vary in cross section are also possible, as demonstrated in the second measuring chamber (240) of FIG. 1. In fact, it is desirable to have the initial portion of the measuring chamber be as small as practical, as this aids in reducing the amount of sample that may be lost from the measuring chamber when diluent initially rushes into the flow directing chamber. Initial diameters of less than 0.5 mm are desirable, preferably less than 0.2 mm. If the entrance to the sample measuring chamber is large, sample is washed up into the chamber when diluent first enters. An unmeasured quantity of sample then flows into the waste chamber as diluent continues to fill the flow directing chamber and flows into both the measuring chamber and the waste chamber. Although this problem cannot be completely eliminated, using a small opening to the sample measuring chamber will reduce sample losses to acceptable levels. A small opening is therefore preferred even when the remainder of the measuring chamber is large (E.G., of non-capillary dimensions).

Additionally, while most measuring chambers will be manufactured to have a fixed volume, it is possible to provide chambers (both measuring chambers and other types of chambers and internal compartments) whose volume can be varied, for example by a closely fitting plunger used to adjust the volume of the chamber prior to use. The internal volume of such an adjustable chamber would be set to the desired value by the user, normally prior to addition of sample to the apparatus.

When sample flows into a measuring chamber, flow stops when sample reaches a stop flow junction, so called because it marks the junction between the early part of the fluid track in which sample flows freely and the later part of the fluid track into which sample does not normally flow until initiation of the dilution process. Since the stop flow junction exists at the limit of the flowpath of the sample, it will be found at one end of the measuring chamber. This same location will normally be the beginning of the receiving chamber (i.e.., when the two chambers are directly connected). However, the stop flow junction can also be present in a fluid passageway connecting the measuring chamber to the receiving chamber.

It should be recognized that flow stop can occur both stably and metastably. A metastable flow stop is one in which flow stops on the macroscopic level but may resume without apparent cause after a time interval of a few seconds to a few minutes. Gradual creep of liquids along container walls or through microscopic or submicroscopic channels resulting from imperfections in the manufacturing process is believed to be the mechanism by which flow starts again once it has stopped. Additionally, small, undetectable vibrations (such as might be caused by persons walking near the apparatus or starting and stopping of nearby equipment, such as air-conditioning units) may also be sufficient to start flow in a metastable situation. However, there is no requirement of absolute stability since the apparatus is designed for addition of a diluent and eventual starting of flow at the stop flow junction. Accordingly, any flow stop which can be sustained for at least 10 seconds, preferably at least one minute, and more preferably at least five minutes, is sufficient for the purposes of this invention.

A stop flow junction is not a traditional valve as it has no moving parts. Rather, this junction relies on back-pressure from the surface tension of the liquid sample to stop flow. This backpressure can be created in a number of ways. For example, backpressure is created when the cross-sectional area of the flowpath increases in a region in which there is contact between the liquid and the container walls (E.G., when a small tube enters a larger chamber or when the cross-sectional area of a channel increases). Greater back-pressure and more consistent operation is achieved when the increase in cross-sectional area of the flowpath is abrupt rather than gradual, particularly when there is a break in capillarity in the sample flowpath. Imperfections in the container walls during gradual widening of chambers may cause liquid to "creep" more on one side than another, thereby avoiding the creation of back-pressure. Liquid can also creep around corners when imperfections are present. Unbalanced forces will also be present when the junction is not horizontal. A horizontal junction, for example, occurs when a vertical tube enters the top horizontal surface of a chamber. If a horizontal tube enters a vertical wall of a container, a vertical junction is present, and the pressure at the bottom of the stop flow junction will be greater than the pressure at the top of the junction, due to hydrostatic pressure caused by the different heights of liquid. Nonetheless, non-horizontal stop flow junctions can be created by reducing the diameter of the smaller channel containing liquid as it enters the larger area, thereby reducing the difference in pressure between the upper and lower portions of the junction.

In many cases, the junction will be formed when a small-diameter measuring tube (i.e., measuring chamber) enters a larger receiving chamber. A small measuring chamber can enter the larger receiving chamber at a right angle or at an angle other than a right angle. The angle between the internal wall of the small tube and the surface of the chamber in the latter case will be different at different locations around the circumference of the junction.

U.S. Pat. No. 4,426,451, which is herein incorporated by reference, describes a number of stop flow junctions that it refers to as "meniscus control means" for use in a device in which there is capillary flow from one zone to another. The stop flow junctions described in that patent can be used in the apparatus of the present invention. However, the patent is not directed to stopping flow when the second zone is not a capillary zone. In contrast to the specific teachings of the patent, which indicate that the walls of the capillary chamber must gradually narrow and gradually expand in order to provide for flow stop, an abrupt widening has been found to be more effective in the practice of the present invention when the second chamber (here the receiving chamber) is not a capillary space. Although it is recognized that imperfections will exist on the molecular level, it is preferred that the junction be as sharp as possible from a macroscopic view point, approaching as closely as possible the ideal junction formed by the intersection of the plane (which can be curved) forming the walls of the measuring chamber with the plane forming the wall of the receiving chamber surface in which the stop flow junction is found. Maintaining a horizontal junction to avoid pressure differentials, reducing the area of the junction, changing the surface of the capillary so as to decrease the hydrophilic character (for aqueous solutions), providing smooth surfaces (rough surfaces encourage creep of liquid along the surface), and providing an abrupt change in cross-sectional area (preferably providing an angle between intersecting surfaces of about 90° or lower) all operate to prevent creep of liquid from one chamber to the other.

In general, for small (capillary-size) junctions, the backpressure will be controlled by the smallest radius of curvature assumed by the meniscus. For example, when a capillary tube with a circular cross-section enters a larger space so that liquid bulges out into the space under hydrostatic pressure, the meniscus will be approximately spherical, and the backpressure ($\Delta p$) is given by the Young-Laplace equation: $\Delta p = 2\gamma/R$, where $\gamma$ is the surface tension of the sample fluid and R is the radius of curvature. See, Miller and Neogi, "Interfacial Phenomena: Equilibrium and L Dynamic Effects", Marcel Dekker, Inc., New York, 1985, and Davies and Riedeal "Interfacial Phenomena", 2nd Ed., Academic Press, New York, 1963. If the fluid meets the surface at an angle greater than 0°, this backpressure will be reduced by a geometric term. The radius, R, will change (become smaller) as the hydrostatic pressure increases, so that the backpressure and hydrostatic pressure balance. As hydrostatic pressure increases, R reaches a minimum value (maximum curvature) determined by the geometry of the device and the contact angle. The corresponding backpressure defines the maximum hydrostatic pressure sustainable by the stop flow junction.

Backpressure is also created when the surface that the liquid contacts changes to decrease adhesion between the liquid and the container wall (for example, when an aqueous sample moves from a hydrophilic to a hydrophobic surface). The surface properties of the various interior surfaces of the device of the invention can and generally will be controlled by various physical and/or chemical treatments. For a discussion of controlling surface properties of similar devices, see commonly assigned U.S. Pat. No. 4,756,884. For example, plastic surfaces can be treated to increase their hydrophilicity. Either the whole apparatus or specific parts can be treated. Alternatively, different parts of the apparatus can be made of different plastics. For capillary flow, contact angles of less than 90° are sufficient, preferably 10°-85° and most preferably 30°-60°. In order to provide these contact angles for aqueous samples, the capillary surfaces will be hydrophilic (at least to some measurable extent). For non-aqueous liquids, a hydrophobic surface would be appropriate. By using a combination of container wall geometry and surface wetability, a backpressure range of from 0 (no change in cross-sectional area or surface adhesion) to 20 cm $H_2O$ and higher can easily be achieved with water as the liquid.

When the backpressure is 0, the location in question is not a stop flow junction. A stop flow junction occurs when there is sufficient backpressure to prevent the flow of sample past a particular point in the flowpath; E.G., from the measuring chamber to the receiving chamber.

A number of diluent application (diluent receiving) sites are disclosed in U.S. application Ser. No. 117,791 and U.S. Pat. No. 4,868,129 discussed above. Any of these diluent application sites can be used in an apparatus of the present invention if desired. In the most preferred embodiment, the diluent application site is an internal vented chamber in the housing that forms the apparatus. Located in the chamber is a rupturable container of diluent. Glass containers are particularly preferred, although frangible plastic can also be used. An access port is provided so that externally applied pressure can be used to rupture the container. A passageway connects the diluent chamber to the flow directing chamber, so that diluent can flow from the ruptured container to the flow directing chamber. Diluent fills the flow directing chamber so that the hydrostatic pressure at the stop flow junction is exceeded and the sample is expelled into receiving chamber along with a portion of the diluent. Excess diluent flows into the waste chamber or remains in the diluent application chamber and/or flow directing chamber.

In the apparatus shown in FIG. 1, the initial diluent chamber (175) is located at a particularly preferred location below the sample application site. This low position for the diluent prevents backflow of diluent through the sample application site. It might appear that such an embodiment would not be capable of providing more hydrostatic pressure at the stop flow junction when diluent is released than was available when sample was added to the sample application site, since the sample application site is gravitationally higher. However, the needed hydrostatic pressure is in fact provided by the diluent and cannot be provided by the sample, because of the flow directing chamber. In the apparatus as described herein, no static column of sample is developed between the sample application site and the stop flow junction when sample is added. The flow directing chamber, and the waste exit, provide a means for draining off sample without allowing that sample to exert pressure on the sample contained in the sample measuring chamber. The effective height of the sample therefore never exceeds the height of the sample measuring chamber. However, the diluent is present in significantly larger quantity than the sample, so that the flow directing chamber is filled along with a portion of the waste chamber and the passage way leading back to the sample application site. Sufficient hydrostatic pressure is therefore developed to break the back pressure at the stop flow junction and expel the sample and diluent into the receiving chamber.

If the diluent application site is above the sample applications site, diluent will flow toward the sample application site through the passageway connecting the diluent and sample application sites. When flow resumes at the stop flow junction, this diluent and any trapped sample in the passageway will flow back into the flow directing chamber. Since, at least in the case of capillary passageways, some amount of sample is likely to remain in the passageway joining the sample application site to the flow directing chamber, there is some difficulty in designing a cartridge to provide a predetermined, reproducible ratio of sample and diluent reaching the receiving chamber. Satisfactory results can be obtained for many reactions by empirical measurement of dilution followed by remanufacture of the cartridge to new specifications and retesting. Design of a cartridge is much simpler, however, by using the lower diluent application site to avoid backflow, as described above.

There are no particular restraints on the geometry of the receiving (mixing) chamber other than that smooth fluid flow be provided for in order to prevent trapping of gas bubbles. Providing entry of sample and diluent into a lower portion of the receiving chamber and providing an upper surface of the receiving chamber that slopes upward toward a vent both aid in avoiding trapped bubbles. It is desirable, however, to ensure that the exit for mixed diluent and sample (if present in the receiving chamber; see below) is located at a distance from the entrance for sample and diluent. If the exit and entrance are located too close to each other, diluent flowing into the chamber while mixture is exiting can reach the exit too early and result in diluent rather than mixture reaching the second measuring chamber. Other provisions can be made to ensure smooth flow of mixture through the exit, such as locating the mixture exit at a low location and the diluent entrance at a high location for diluents that are lighter than the mixture of sample and diluent (and vice versa).

The vents used in the various chambers of the device can merely be a small hole terminated by a stop flow junction in order to avoid exit of liquid from the device or can be a more sophisticated vent designed for gas exit without exit of liquid E.G., a microporous, hydrophobic plug capable of passing air but not hydrophilic liquids). Stop flow junctions can also be placed in the early portion of a long vent to prevent a relatively large quantity of liquid from entering the vent from the the vented chamber. A vent or other means to allow exit of trapped air is provided at every location in the apparatus in which the trapping of air would interfere with the passage of liquids between the various chambers and/or channels of the device.

Although there is no theoretical upper limit on the size of samples that can be measured and diluted in this first step (or later steps) using an apparatus of the invention, the method and apparatus are particularly suitable for measuring and diluting small quantities of liquids. Accordingly, the sample measuring chamber will generally have a volume of from 0.1 $\mu$L to 100 $\mu$L, preferably 1 $\mu$L to 30 $\mu$L, and most preferably 3 $\mu$L to 10 $\mu$L. The receiving chamber, which acts to limit diluent volume and fix the ratio of sample to diluent, generally has a volume of from 3 $\mu$L to 1000 $\mu$L, preferably 10 $\mu$L to 300 $\mu$L, and most preferably 30 $\mu$L to 100 $\mu$L, thereby providing dilution ratios of from $10^4$:1 to 3:1, preferably $10^3$:1 to 10:1, and most preferably 100:1 to 10:1. Channels through which capillary flow will take place will usually have opposing walls spaced in the range of about 0.01 mm to 2 mm, more usually about 0.1 mm to 1 mm. The capillary spaces can be tubular (which does not necessarily imply a circular cross-section but can be square or other regular shapes) or can represent the space formed by flat plates and side walls with the side walls being spaced further apart than a capillary distance. A tubular chamber with at least one flat side (E.G., a square cross-sectional area, a rectangle with adjacent sides differing in length by no more than a factor of 1:2 to 1:4, or a semicircular chamber) are preferred for ease of manufacture in cases where channels are being formed by the joining of two adjacent surfaces, one of which can be flat.

It should be recognized that statements in this specification indicating upper and lower limits of ranges are to be taken as individually designating a series of upper limits and a series of lower limits which can be utilized in any combination. For example, a typical upper limit and a preferred lower limit may be used in combination to define a range of intermediate preference.

The apparatus as described above provides for a single dilution of a sample with a diluent. Any apparatus that carries out a dilution in the manner described is considered to fall within the scope of the present invention, whether the dilution occurs by itself or as part of additional operations that occur in the device. For example, other operations can be carried out on an original sample so as to provide a mixture. This mixture is then the "sample" that is later diluted. Alternatively, provision can be made for other operations to take place on the mixture formed in the manner described above.

In particular, the present inventors contemplate providing serial dilution and mixing capabilities using a mixture measuring and isolating chamber hydrostatically connected to the mixing chamber and a valve controlling passage of fluids from the mixing chamber to the mixture isolating chamber. The first dilution takes place as indicated above during which time the indicated valve is closed to prevent escape of liquid from the mixing chamber. After the first mixture is formed, the valve controlling flow to the mixture isolating and measuring chamber is opened, and fluid flows from the mixing chamber under the influence of hydrostatic pressure and/or capillary attraction. The portion of the mixture isolating chamber into which the mixture flows is smaller in volume than the total volume of mixed sample and diluent. This volume is determined by the geometry of the chamber, the amount of hydrostatic pressure available from liquid in the mixing chamber, and any capillary forces that are present. U.S. Pat. application Ser. No. 117,791, described above, describes various geometries that can be provided for a mixture isolating chamber depending on whether the intent is to carry out a second dilution in the original mixing chamber or to transport the isolated portion of the mixed sample and diluent to another location for further dilution and/or analysis. Any apparatus that carries out a single dilution as described above and a second dilution as described in the prior application will fall within the scope of the present invention.

However, a particularly preferred embodiment of the present invention is directed to an apparatus in which serial dilutions are carried out, both of which fall within the scope of the single-dilution invention set forth above. In such embodiments, the mixture isolating chamber will comprise the same types of chambers and passage ways as described previously, with the exception that they will operate on the mixture as a sample rather than on an initially obtained sample.

Any type of valve that will control the passage of liquids between chambers and/or channels can be used in the apparatus of the present invention. Simple valves that can be actuated to move between an open and a closed position by the application and release of a simple external force are preferred.

Examples of such valves include resilient blocking members that are present in or adjacent to a liquid flowpath. For example, a resilient blocking member can be present in a converging or diverging pathway so that the narrow portion of the pathway is blocked by the resilient blocking member when the blocking member is in its normal position. Application of force in a direction generally away from the restricted portion of the flowpath and toward the wider portion of the flowpath will open the valve by moving the blocking member away from the narrow walls of the flowpath. Alternatively, a normally open valve can be provided which is blocked by movement of a resilient blocking member to a location that cuts off flow of liquid. Specific examples of such valves are set forth in more detail below.

Other examples of such valves include sliding pins closely engaging a channel that laterally traverses a fluid flowpath. The pin has a segment capable of obstructing flow through the flowpath when the pin is in a first position and a segment capable of allowing flow through the flowpath when the pin is in a second position. Examples of such pins include rectangular pins having a flowpath channel between two opposite faces of the pin, the flowpath channel being out of register when the block is in a closed position and in register with the principal flowpath when the block valve is open. Pins with circular cross-sections can be used by providing an obstructing segment of the pin that snugly engages the channel in which the pin fits and obstructs the flowpath when the pin is in a closed position. A smaller cross-sectional area (such as is present in the handle of a dumbbell) provides an annular flowpath around the smaller, central portion of the pin when the pin valve is in the open position.

A resilient member can be provided to bias the pin into either the closed or the open position. A force acting on the pin can then slide the pin to a second location so that the pin valve is in the alternate position.

In preferred embodiments, access for the application of an external force on the pin is provided so that the pin can be moved between its two positions. For example, a section of the pin that protrudes externally from the apparatus can be provided so that a force acting parallel to the sliding axis of the pin can move the pin from its first biased position to a second position by acting against the direction of the biasing force. Alternatively, an aperture leading from a face of the pin opposite the biasing force to the external environment can be provided. Externally applied pressure, such as from compressed air or a finger of an external apparatus that enters the aperture, can be used to slide the pin between its open and closed positions. A resilient seal can be provided to prevent loss of liquid through the aperture while allowing force to be applied to the pin. Such seals can also be provided for the resilient blocking members described above.

The valves that can be used as integral parts of a cartridge of the present invention are not limited to those specifically exemplified here. Rather, any valve can be used that can control the flow of liquids through small flowpaths, such as flexible walls (E.G., latex) of a flowpath that can be compressed to restrict flow of liquid through the flowpath. Additionally, a dissolvable barrier can be provided in instances where an initially closed valve will be opened once and then maintained in the open position.

It is also possible to provide an external valve. For example, a flowpath through which capillary flow occurs can be blocked by closing an external vent. When the external vent is closed, liquid cannot enter the capillary pathway because of air or other gases in the capillary pathway. Opening the vent allows liquid to enter the capillary pathway. If the vent is closed while liquid is contained in the capillary pathway, the isolated liquid can later be used for other manipulations.

Valves consisting of external vent controls can be used in any situation where flow occurs through a capillary pathway (so that trapped air is effective to control flow of liquids) and where no free liquid that might leak is stored in the cartridge prior to use. Encapsulated liquid (E.G., in glass ampules) can be present in devices using external vent controls. In many cases it is desirable to store premeasured diluents (which can contain reagents) in the cartridge when the cartridge is delivered to an end user. Internal mechanical valves or rupturable barriers are preferred for such uses in order to prevent accidental leakage.

By providing valves that can be operated by a simple externally applied force, a cartridge-like device can be provided in which the valves are opened and closed in a predetermined manner by an analytical device into which the cartridge is inserted. This analytical device can contain various optical and/or other types of sensors for detecting the presence of liquids or analytes in various mixing and/or measuring chambers of the cartridge in addition to providing means for opening and closing the valves and is therefore sometimes referred to in this specification as a monitor.

The apparatus of the present invention can be designed for use with a particular assay or can be designed and prepared as an apparatus in which multiple assays can be carried out, depending on the order in which various valves are opened and closed and the contents of the various diluents, which can contain reagents for the development of a detectable signal (E.G., a color reaction) that depends on the presence of an analyte in the sample.

Reagents can be provided at various locations in the device. Incubation times can be controlled by either manual operation of valves or by a mechanically or electronically stored program in the monitor into which the cartridge is inserted. The program can be selected from a bar code on the cartridge. The program would control the order and timing of opening and closing valves. The programmed device would contain solenoids or other means for providing force to open and/or close valves or rupture containers containing diluent. In embodiments in which flow through a capillary pathway is being controlled by the opening and closing of a vent, a movable sealing pad that is capable of closing the vent will form part of the external programmed device into which the cartridge is inserted.

The monitor is also capable of detecting correct operation of the cartridge by providing sensors that detect the presence of liquids at various locations in the fluid pathways of the cartridge and comparing the signals provided by the sensors with the signals that would be produced during proper operation of the cartridge. Automatic detection of proper operation is desirable when the cartridge is in the hands of an unskilled user, which is a desired end use of the cartridge. For example, if the user must apply a drop of blood (as the sample) to the sample application site, several problems can occur. Some patients have trouble obtaining a drop of blood of sufficient volume. For example, if proper operation of the cartridge requires 25 μl of blood and only 20 μl is added to the sample application site, the sample measuring site may not completely fill. If diluent is then added automatically (such as after a preselected time), the dilution will be greater than desired, and an incorrect result will be obtained.

The cartridge of the present invention provides suitable locations in the flow paths, particularly by providing flow directing chambers, to allow adequate monitoring of this and other potential problems. A light source and detector can be provided in the monitor so that they are located on opposite sides of the flow directing chamber when the cartridge is registered in the monitor. By detecting light that passes through the flow directing chamber at different location, different aspects of sample (and diluent) flow can be detected.

For example, sample entering the flow directing chamber can be detected by detecting light at a location adjacent the sample entrance. This allows initiation of timing of later operations. For example, the sample can be incubated with a reagent located in the sample measuring chamber for a specified amount of time without requiring any operation on the part of the user other than applying the sample.

By using a flow directing chamber with two spaced-apart exits leading to the sample measuring and waste chambers, locating the sample entrance so that sample reaches the sample measuring chamber entrance before it reaches the waste chamber entrance, and locating the light path for the sensor between the two exits, two different measurements of system operation can be carried out with a single sensor. Since sample fills the measuring chamber before reaching the waste exit, detection of sample indicates that the sample measuring chamber has filled. Continuing to monitor the same location allows detection of complete emptying of the flow directing chamber, as sample flows out of the flow directing chamber and into the waste chamber. Dilution can then be properly timed to avoid accidental addition of diluent while sample is still present in the flow directing chamber, which would lead to too low a dilution as extra sample was swept into the receiving chamber along with the diluent. Other problems that might lead to sample in the flow directing chamber, such as a clogged waste exit or too large a sample, could also be detected.

A series of Figures is provided to illustrate a number of embodiments of the invention. The embodiments shown in the Figures are not intended to be comprehensive, and numerous other embodiments within the scope of the appended claims will be apparent to those of ordinary skill in the field of the invention.

Figures 2A, 2B, 2C, 2D:
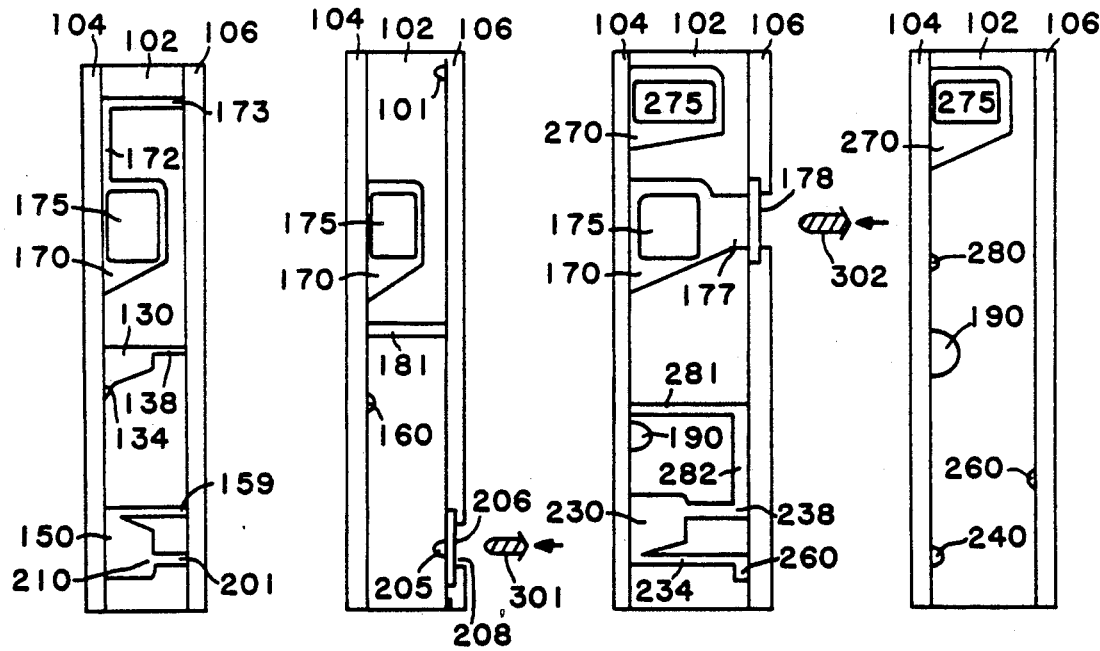
FIG. 2 is a series of four vertical cross-section of the embodiment of FIG. 1 taken at locations A—A through D—D of FIG. 1.

FIG. 1 is a plan view from the front of a first embodiment of the invention in which lines A—A, B—B, C—C, and D—D show the location of the cross-sectional view shown in FIG. 2. As shown in FIG. 2, housing 100 is prepared from three separate pieces, a central base member No. 102 and two cover plates 104 and 106. Chambers formed in the front face of base member 102 (the left side of the cross-sectional view shown in FIG. 2) are shown by dashed lines in FIG. 1. Through connections, which are generally holes passing from one face to the other, are shown by circles in FIG. 1. All such passageways would be visible in embodiments prepared from transparent plastic, as described in U.S. Pat. No. 4,756,844. However, it is also possible to prepare the cartridge from an opaque material if provisions are made for light paths at the appropriate locations.

The apparatus shown in FIG. 1 is capable of carrying out two dilutions serially. Parts of the apparatus associated with the first dilution are numbered from 110 to 190. Parts of the apparatus associated with the second dilution are numbered from 205 to 282. Where two parts perform the same function in the first and second dilutions, the last two digits of the identifying number are the same. Parts of the apparatus associated with the housing are numbered from 100-106, and parts of the monitor that interact with the cartridge shown in FIG. 1 are numbered 300 and above. The apparatus will be described by reference to the indicated numbers while following a sample through a series of two dilutions in the apparatus.

A sample is added initially to sample application site 110. The sample flows down passageway 120 to flow directing chamber 130, entering the chamber at an entrance 136 in the upper left hand portion of the chamber as shown in FIG. 1. Passageway 120 has capillary dimensions, while chamber 130 is sufficiently large so as not to support continued capillary flow. Sample flows by gravity down the left-front edge of chamber 130 and encounters entrance 132 to measuring chamber 140. Sample continues to flow down measuring chamber 140, which is of capillary dimensions. Sample flow stops when the leading edge of the sample reaches stop flow junction 145 at the junction between sample measuring chamber 140 and receiving chamber 150. Vent 159, located in a upper portion of chamber 150, is connected to common vent 101 to allow exit of gases from chamber 150, thereby allowing flow of sample into capillary sample measuring chamber 140.

Excess sample continues to flow down passageway 120 into flow directing chamber 130. Since sample can no longer enter measuring chamber 140, sample accumulates at the bottom front edge of the chamber since the floor of the chamber slopes downward toward the front of the chamber (see FIG. 2, part A). When excess sample reaches waste exit 134, waste channel 160, which is of capillary dimensions, draws sample into waste chamber 190. Since waste exit 134 is at a gravitational low point of chamber 130, excess sample continues to flow into waste chamber 190 until all excess sample has been drained from chamber 130.

At this time, rupturable container 175, which is located in diluent application chamber 170 is ruptured by a mechanical finger (302; shown in FIG. 2, part C) inserted through access port 177. Rupturing of container of 175 is discussed in detail below. Diluent flows through channel 180 along the front face of the apparatus, passes through channel 181 to the back face of the apparatus, and enters flow directing chamber 130 through entrance 138. Sufficient volume of diluent is provided to fill flow directing chamber 130 and at least a portion of waste chamber 190 while sufficient diluent remains in chamber 170 to provide a hydrostatic pressure at stop flow junction 145 sufficient to initiate flow, so that the sample trapped in measuring chamber 140 is expelled into receiving chamber 150, followed by diluent. Diluent fills chamber 150, thereby providing a fixed ratio of sample to diluent in the chamber.

Mixing in chamber 150 can be provided by a number of techniques, such as are described in a co-pending application entitled "Reciprocal Mixing Cartridge," now U.S. Pat. No. 5,028,142. It is preferred to begin mixing the sample and diluent as they enter the chamber so that any mixture entering the vent will have approximately the same composition as the mixture remaining in the chamber. However, the volume of the vent is sufficiently small so that negligible error results. Additionally, it is possible to include a separate stop flow junction in the vent to prevent excess exit of liquid, should higher accuracy be desired. Such a stop flow junction and the vent to the mixing chamber is a part of the apparatus relating to the second dilution, as discussed below.

Exit 210 in receiving chamber 150 serves as the entrance for mixture into the second dilution portion of the apparatus. During this initial first dilution, however, passage way 205 is blocked by a valve shown in detail in FIG. 2, part B, below. When the valve is open, a portion of the mixture flows through exit 210 and channels 205 and 220 to a second flow directing chamber 230, referred to herein as the mixture flow directing chamber. The floor of chamber 230 slopes downward from the left side of the chamber and from the back of the chamber to a small area at the right front corner of the floor of the chamber. At this point mixture measuring chamber 240 is connected to mixture flow directing chamber 230 at junction 232. Mixture measuring chamber 240 terminates at stop flow junction 245 where chamber 240 intersects with mixture receiving chamber 250.

Since the mixture in receiving chamber 150 is under hydrostatic pressure from diluent located in the various pathways leading to chamber 150, mixture and eventually unmixed diluent can continue to flow into mixture flow directing chamber 230 until the hydrostatic pressure is equalized. A mixture waste chamber and mixture waste pathway exiting chamber 230 could be provided in a manner similar to waste chamber 190 and passage way 160 in the first dilution pathway. However, in the embodiment shown in FIG. 1, an alternative method is provided for controlling flow. Since the purpose of the apparatus is to mix small samples with diluents that can contain reactants and measure the resulting reaction in the receiving chambers, the apparatus shown in FIG. 1 will normally be inserted into an apparatus in which such measurements can made. Optical measurements are common and are the preferred type of measurement for an apparatus shown in FIG. 1. A light source and a detector are located in the monitor so that the light impinges on the desired location in the receiving chamber, passes through the receiving chamber and the material enclosed therein, and impinges on the detector located at the other side of the cartridge. This is accomplished by inserting the cartridge into a chamber on the surface of the monitor so that all of the parts are placed into proper registration with each other. The present invention requires nothing new in the way of light sources, detectors, and registration means, since all spectrophotometers that engage cuvettes and carry out light measurements there through provide the necessary detection and registration systems.

However, the monitor can be easily modified by providing additional light sources and detectors to detect the presence of the fluid at various points in the fluid pathways throughout the cartridge, as was discussed above. In this specification such components are called system control components since they represent a means by which the monitor can verify whether sample, the diluted mixture, or the like have reached the proper points in the fluid pathway in the proper sequence and at the proper time. For example, light sources and detectors can be placed at opposite sides of the cartridge so that the detector measures light passing through the mixture measuring chamber 240 near stop flow junction 245. As shown in FIG. 1, this portion of the measuring chamber can be made small relative to other portions of the measuring chamber in order to minimize error. When the detector indicates that liquid has reached the end of measuring chamber 240 adjacent stop flow junction 245, the valve that allows mixture to enter through access port 210 can be closed. Flow through the mixture measuring chamber will then stop when the meniscus of the mixture reaches stop flow junction 245. Excess mixture remaining in mixture flow directing chamber 230 can then be drained off into mixture waste exit 260, which as shown in FIG. 1 is a capillary channel.

Providing system controls to close the valve located in passageway 205 and providing a capillary waste channel 260 obviates the need to have a large, gravity-fed waste chamber located below the level of mixture flow directing chamber. This is desirable in the device shown in FIG. 1 since a preferred technique of mixing is to use a magnetically driven mixing member in the two receiving chambers. Eliminating a relatively large waste container at the bottom of the cartridge allows the receiving chambers to be located closer to the bottom of the cartridge, thereby reducing the distance between the mixing member and the receiving chambers and the driving magnets. Capillary waste chamber 260 will draw off excess mixture until all excess mixture has been removed from mixture flow directing chamber 230.

At this time, a second diluent in rupturable diluent container 275 contained in diluent chamber 270 is broken in the same manner as diluent container 175. Diluent therefore becomes available at diluent application site 270, flows through channels 280, 281, and 282, and enters mixture flow directing chamber 230 at entrance 238. As with the first dilution, the hydrostatic pressure provided by the diluent as it fills chamber 230, waste channel 260, and vent 239, overcomes the back pressure at stop flow junction 245. Diluent is then expelled from mixing measuring chamber 240 into mixture receiving chamber 250. Diluent also flows through mixture measuring chamber 240 into mixture receiver chamber 250, expelling trapped air through vent 259. Since vent 259 would normally vent to the external atmosphere at the top of housing 100, a stop flow junction is provided in chamber 255 to minimize the amount of mixture and/or second diluent entering vent 259. Mixing takes place in receiving chamber 250 in the same manner as in receiving chamber 150.

FIG. 2 shows a series of cross-sectional views at different locations shown in FIG. 1. The cross-sectional view shown in part A of FIG. 2 intersects a number of channels, chambers, and vents associated with the first dilution. As mentioned previously, the apparatus is assembled by attaching cover plates 104 and 106 to central body member 102 in which the various chambers and passage ways are formed. In all parts of FIG. 2, the left sides of the figure represents the front face of the embodiment shown in FIG. 1 and the right side represents the back face.

Starting at the top of part A of FIG. 2 and moving down, one sees passageway 173 leading from the front face to the back face of body member 102. Because the various fluid and venting passageways shown in FIG. 1 must cross over each without intersecting, through passages such as 173 allow fluid pathways to be switched from one side of the other to avoid interference. An example of this can be seen in FIG. 1 in the fluid pathway which delivers the second diluent from diluent receiving site 270 to mixture flow directing chamber 230. This flow pathway must cross over both waste chamber 190, which occupies the front face of the apparatus, and vent 103, which occupies the back face. This is accomplished by providing an initial channel 280 along the front face of body member 102 until the passage way crosses over vent 103. At this point through passageway 281 switches the fluid pathway to the back face of body member 102. There channel 282 passes behind waste chamber 190 until it reaches an appropriate location behind mixture flow directing chamber 230. Passageway 238 then leads to the flow directing chamber which is located on the front face of the apparatus. The manner that this is accomplished is seen near the top of part A of FIG. 2 where vent 172 connects chamber 170 to cross vent passage way 173, which transfers the vent path to the back face of the apparatus. At this point a connection is made to common vent passageway 101, which is visible in FIG. 1 but not in part A of FIG. 2.

Also visible in part A is passageway 138, which provides access for first diluent to mixing chamber 130 and enters chamber 130 from the back face of the device. Exit 134, by which excess sample enters waste channel 160, can be seen at the bottom corner of chamber 130.

The high location of vent 159 at an upper corner of mixing chamber 150 is evident near the bottom of part A of FIG. 2. Access port 210 leading into channel 201 that forms the first portion of the channel by which mixture is transported to the second dilution system can also be seen in chamber 150.

Part B of FIG. 2 shows a number of minor features in the upper portion of the Figure, such as common vent 101, container 175 located in chamber 170, through passageway 181, and waste channel 160.

A particular valve embodiment is seen in the lower right hand portion of this Figure. Channel 205 is a mixture flow channel that connects mixing chamber 150 to mixture flow directing chamber 230. A thin flexible membrane 206 is held in place by back plate 106 at aperture 208 located directly behind channel 205. A plunger 301 located in the monitoring device into which the cartridge is inserted is adjacent aperture 208 when the cartridge is registered in the monitor. This plunger is under the control of various sensors in the monitor and is moved to the left in the direction of the arrow when the monitor receives the signal from the monitor. Such a signal might be given, for example, by insertion of the cartridge into the monitor. The end of plunger 301 is shaped to fit channel 205 so that when plunger 301 is urged to the left, flexible membrane 206 is forced to fit tightly into channel 205, thereby blocking the channel. Release of the leftward-acting force on plunger 301 after mixing has been accomplished in receiving chamber 150 then allows mixture to flow through channel 205 into the remainder of the apparatus.

Part C of FIG. 2 shows a vertical cross section through the embodiment of FIG. 1 at line C—C. Second diluent container 275 can be seen located in diluent chamber 270. This view intersects chamber 170 at the location of aperture 177. This aperture, which leads to the back face of the cartridge, is covered by flexible seal 178. Plunger 302, located in the monitor, can be urged leftward in the direction of the arrow at an appropriate time under control of the monitor. Sealing member 178 is sufficiently flexible to allow force to be applied by plunger 302 on container 175, thereby rupturing container 175 and releasing diluent into diluent chamber 170. Release of the biasing force on plunger 302 moves plunger 302 back to its original position (as shown) without rupturing seal 178.

In the lower portion of part C of FIG. 2 can be seen waste chamber 190 and a number of chambers and passages associated with the second dilution. Through channel 281 and channel 282 along the back face of body member 102 provide access for the second diluent to mixture flow directing chamber 230, through which diluent enters at passage way 238. Through passageway 234 leading to capillary waste channel 260 is also visible.

Part D of FIG. 2 shows a vertical cross section taken at line D—D of FIG. 1. Second diluent container 275 and diluent chamber 270 are again visible as is waste chamber 190. Channel 280, which is part of the pathway leading from the second diluent chamber to mixture flow directing chamber, is also visible, as are sections of capillary waste chamber 260 and mixture measuring chamber 240.

Figure 3:
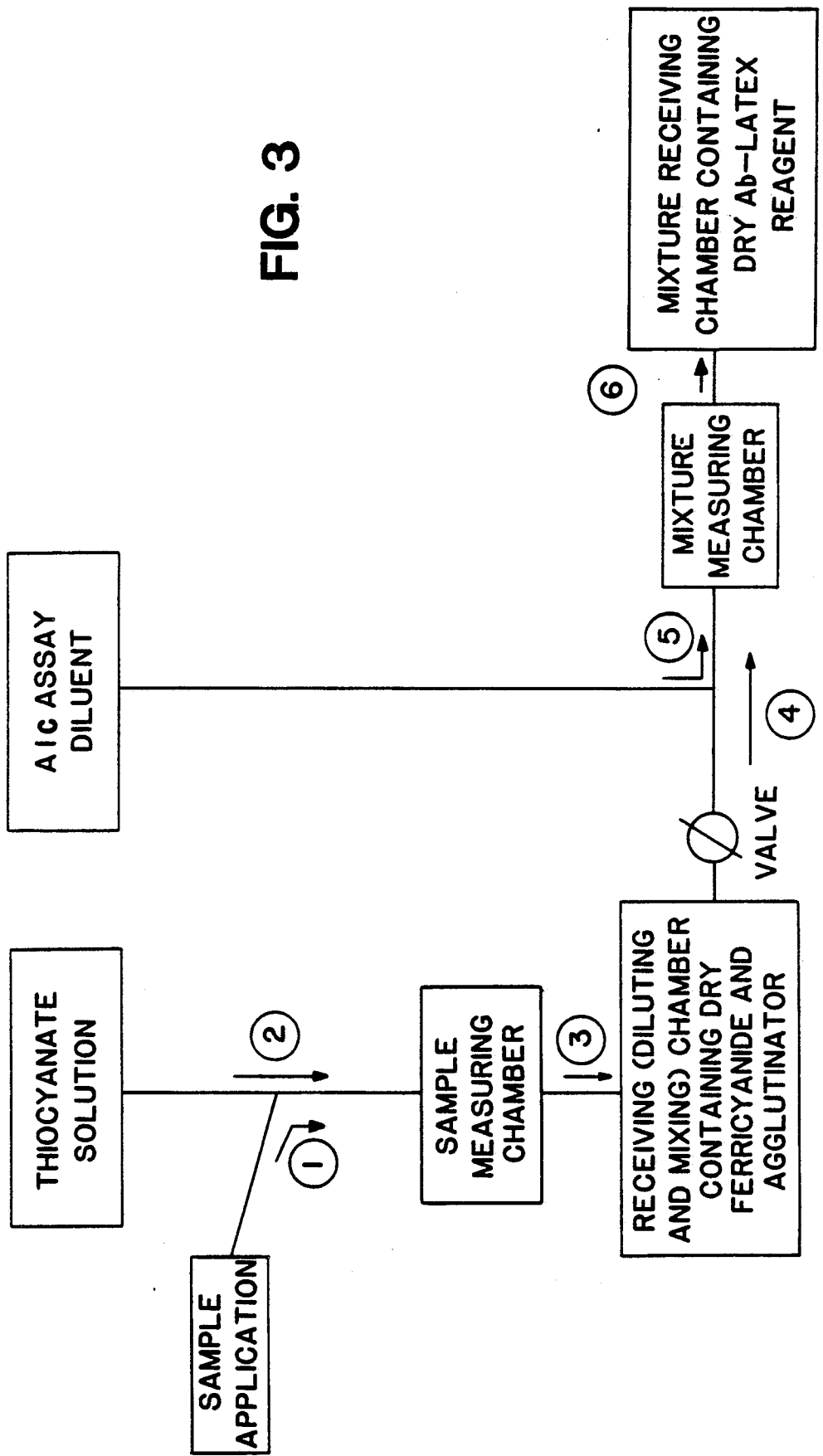
FIG. 3 is a schematic diagram of a specific analysis scheme used in a device of the invention.

FIG. 3 is a schematic diagram showing reagents that would be used with a cartridge of the type as shown in FIGS. 1 and 2 to carry out a specific diagnosis. Hemoglobin A1c, a minor hemoglobin component, is present in normal persons but increases in the presence of hypoglycemia. Hemoglobin A1c measurement therefore provides an assessment of long-term insulin control in diabetics. An analysis requires an initial mixing of whole blood with a first set of reagents to determine total hemoglobin content followed by determination of hemoglobin A1c content on an aliquot of the first mixture. The process steps are shown schematically in FIG. 3 and are described below as they would occur in the apparatus of FIG. 1.

A sample from an unmeasured blood drop will be applied to sample application site 110. Sample will flow into measuring chamber 140 through sample flow directing chamber 130. Flow of blood stops at the junction chamber 140 mixing/reading chamber 150. When container 175 is broken, thiocyanate solution will flow through measuring chamber 140 into mixing chamber 150, pushing the blood sample ahead of itself. The mixture of blood and thiocyanate solution will fill mixing chamber 150. Homogeneous mixing of blood and thiocyanate will now occur, driven by a reciprocating mixing plate, and the ferricyanide and agglutinator reagents coated on the walls of mixing chamber 150 (at different locations) will dissolve. After about 1 minute, the blood will be lysed and the hemoglobin denatured. At this time, the total hemoglobin will be measured by reading absorbance at 540 nm and 800 nm using a light source and detector that are present in the monitor into which the cartridge has been inserted.

The valve in channel 205 will then be opened to allow a portion of the mixture to flow into the measurement (mixture isolation) chamber system. When mixture reaches the end of mixture measuring chamber 240, the vent is closed to prevent excess mixture from filling flow directing chamber 230 and expelling mixture from the mixing chamber by hydrostatic pressure. Once the mixture flow control 230 chamber has been drained by capillary drain 260, diluent container 275 is broken, allowing A1c diluent to flow into the dry antibody-latex reagent chamber 250, resuspending the reagent (which is coated on the chamber walls of chamber 250), after displacing the sample of denatured blood (i.e., the isolated mixture) from mixture measurement chamber 240 into the mixing/reaction chamber 250. The denatured blood/reagent mixture will then be mixed and assayed for hemoglobin A1c by measurement of the change in turbidity over about 30 seconds. Turbidity increases as a result of agglutination of antibody-coated latex particles, the antibody being specific for hemoglobin A1c.

The entire apparatus shown in FIGS. 1 and 2 would be approximately 10 cm high and less than 15 cm wide with body member 102 being about 1 cm in thickness. The cartridge can readily be prepared in other sizes to carry out other analytical measurements.

Expanded perspective views of two flow directing chambers of the invention are shown in FIGS. 4 and 5, in which edges that would be visible from the point of view shown are indicated by solid lines and edges that are seen through the chamber are indicated by dotted lines. FIG. 4 resembles chamber 130 of FIG. 1 and is numbered accordingly. Chamber 130 is essentially a truncated cube or wedge with all opposed faces parallel except the top and bottom faces. Height X of the back is smaller than height Y of the front face. In the bottom front corners of chamber 130 can be seen exits 132 leading to the measuring chamber and 134 leading to the waste chamber. In the corner directly above exit 132 (the sample measuring chamber entrance) is entrance 136 for sample, a passageway leading from the sample application site. Vent 139 and diluent entry 138 are visible in the upper back corners of the chamber. Passage of fluids through the chamber is indicated by arrows and Roman numerals. Arrow I shows initial flow of sample after arriving in chamber 130 through entrance 136 and flowing down the left front corner of the chamber to sample measuring chamber entrance 132 under the influence of gravity. When the sample measuring chamber is filled, flow continues across the bottom front face of chamber 130 to waste exit 134 as shown by arrow II. Since exit 134 is at a gravitationally low point of chamber 130, excess sample will continue to be drawn out of chamber 130 until all sample exits the chamber, except for any small amount retained by surface tension resulting from contact with the sample in the measuring chamber at measuring chamber entrance 132. However, any such amount will be small and relatively reproducible, since the apparatus of the invention is designed for use with samples of a particular type that will have relatively similar if not identical surface tension characteristics.

Location A shown at the front lower face of chamber 130 between exits 132 and 134 is a preferred location for measuring transit of sample, as previously indicated. If a detector is located in the monitor so that light passing through the back face A' of chamber 130 is detected as it passes through region A on the front face, sample passing along path II will be detected. Thus, initial appearance of sample at location A will indicate that sample has filled the measuring chamber and has started flowing across path II. When sample disappears from location A, the dilution process can be initiated. In the rare case where a slightly large sample is used, so that the sample fills the sample measuring chamber and overflows exit 132 slightly into chamber 130 but not sufficiently so that sample reaches exit 134, the detector at location A will prevent automatic dilution of this incorrect sample size. When the correct signal is received to indicate proper measurement of sample, diluent enters through entrance 138 and flows along the path shown by arrow III, thereby completing the dilution process as previously described.

As is apparent from the operation as described for FIG. 4, it is desirable that waste exit 134 be of capillary dimensions at least in the initial section of the passageway to aid in wicking sample from the chamber as soon as sample reaches exit 134.

It can be seen from FIG. 4 that location A intersects the bottom edge of the chamber. Such a location is desirable because slight differences in registration may occur when the cartridge containing the chamber is inserted into a monitor, due to the very small sizes of chambers, as previously described. If the location is selected so as to intersect the bottom edge of the chamber, cartridges that fit slightly higher or slightly lower in the registration means of the monitor will still have the light path intersect the bottom edge, thereby insuring that sample will intersect the light path as sample travels along the bottom edge of the chamber. If desired, back face A of the chamber can be molded during the chamber-forming process so as to form a lens that aids in directing light to the correct location.

FIG. 5 shows a second embodiment of a control flow chamber similar to the second flow directing chamber shown in FIG. 1. The chamber again resembles a truncated cube, but the bottom face slopes toward one corner with three equal corner heights indicated by X and one longer corner indicated by Y. The top face is horizontal and the bottom face of the chamber slopes downward to the Y corner. The various entrances and exits from the chamber are numbered in accordance with the designation set forth in FIG. 1 for chamber 230. Accordingly, sample enters through entrance 236 and flows along path I to the lower right corner of chamber 230. In contrast to the embodiment shown in FIG. 4, path I encounters waste exit 234 before encountering exit 232 leading to the measuring chamber. However, exit 234 is sized in comparison to entrance 236 and exit 232 so as not to be able to pull all of the sample (here normally the mixture) along path IIa to the waste chamber. Sufficient sample is therefore available to enter the measuring chamber through port 232 along path IIb. When the measuring chamber is filled, excess sample continues along path IIa until the chamber is emptied. Diluent then enters through entrance 238 and flows along path III to complete the dilution process as previously described.

A light source and detector can be provided in the monitor so that the light path passes through location A in a manner similar to that described above for FIG. 4. However, in FIG. 5 location A is between the sample entrance and the two exit ports in comparison to FIG. 4, where it was located between the two exit ports. However, this location can still be used to detect entry of sample into the chamber and, when combined with a timing circuit, can be used to determine whether sample has filled the sample measuring chamber, since the apparatus is designed for use with a particular type of sample (E.G., whole blood), and the time required to fill the measuring chamber will therefore be relatively constant. Depletion of sample from the chamber can also be detected, as previously described.

The cartridges of the invention are typically prepared from molded plastic as described in U.S. Pat. No. 4,756,844, the only principal differences between the production methods described in the patent and the production required for the present apparatus being in the mold used to form the various chambers. As indicated in the patent, plasma etching can be used to improve flow characteristics through the various capillary pathways, since most molding plastics are hydrophobic and need to be rendered hydrophilic for reproducible capillary flow to occur.

It is now been discovered that superior results are obtained by masking part of the capillary tracks and chambers so that not all of the interior surfaces are etched. For example, the first stop flow junction 136 of the embodiment shown in FIG. 1 and FIG. 2 occurs at a corner of chamber 130 formed by face plate 104 and body member 102 (also see FIG. 4). The sudden widening of the fluid passageway as it enters chamber 130 acts to create a stop flow junction. However, a continuous face and therefore continuous flow path is present along face plate 104 as passageway 120 enters chamber 130. Plasma etching of pathway 120 is important to maintain capillary flow through the pathway. However, if the intersection of pathway 120 and chamber 130 is masked during the etching process, the region of face plate 104 at the stop flow junction will be hydrophobic, thereby improving the operating characteristics of the stop flow junction. Similar masking of surfaces in other locations where capillary flow or entrapment is not desirable, such as other stop flow junction or corners and edges of chambers that tend to retain liquids in undesired locations, also can be used to provide improved operating characteristics.

In a similar manner, selective plasma etching of chambers can be used to prevent reagent spread during application of reagents to surfaces in the chambers. Reagents are typically added to a cartridge of the invention in the form of a solution which is then dried to provide a stable reagent composition. When liquids are added to etched surfaces, they tend to spread out in thin films and occupy a relatively large area of the surface. This can lead to intermingling and premature reaction of reagents if two reagents need to be applied in a small area, such as a mixing chamber. If a section of a surface is not plasma etched, however, reagent applied in liquid form will tend to remain in droplets in the applied location rather than spreading out. Smaller chambers can used because of less spreading of reagents by selectively masking the surfaces to which reagents will be applied before plasma etching.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A dilution and mixing cartridge for automatically measuring and diluting a liquid sample with a liquid diluent, comprising:
in a housing,
sample receiving means for receiving a sample,
a flow directing chamber, comprising a first internal chamber in said housing,
sample flow means for delivering sample from said sample receiving means to said flow directing chamber,
diluent receiving means for receiving a diluent,
diluent flow means for delivering diluent from said diluent receiving means to said flow directing chamber, a receiving chamber, comprising a first vented internal chamber in said housing having a first volume, a measuring chamber, comprising a second internal chamber in said housing having a second volume smaller than said first volume, wherein said measuring chamber connects said flow directing chamber to said receiving chamber and said measuring chamber is capable of delivering sample and diluent from said flow directing chamber to said receiving chamber solely by capillary and gravitational forces, a stop flow junction located at the end of said measuring chamber, wherein said stop flow junction with conforms to the surface tension characteristics of said sample so as to provide sufficient back pressure resulting from contact between said sample and wall means of said housing at said stop flow junction to prevent sample from flowing through said stop flow junction in absence of diluent but allowing flow through said stop flow junction when said diluent receiving means receives diluent and diluent enters said flow directing chamber, and waste means for emptying said flow directing chamber after sample has entered said flow directing chamber and said sample has filled said measuring chamber, wherein said waste means operates by capillary and gravitational forces, whereby diluent added to said diluent receiving means flows through said flow directing chamber and expels sample from said measuring chamber into said receiving chamber, thereby causing a fixed ratio of sample to diluent to be delivered to said receiving chamber.

2. The cartridge of claim 1, wherein said flow directing chamber comprises:
(1) an exit for said measuring chamber and said waste means at gravitationally low points in said flow directing chamber, and
(2) entrances for said sample and diluent flow means gravitationally above said exit and said waste means.

3. The cartridge of claim 2, wherein said entrance for said sample flow means is located above said measuring chamber exit and positioned so that flow of sample into said flow directing chamber reaches said measuring chamber exit before reaching said waste means.

4. The cartridge of claim 2, wherein said flow directing chamber comprises a floor sloping downward to said exit and said waste means.

5. The cartridge of claim 2, wherein said waste means comprises an exit in said flow directing means having a cross section smaller than the cross section of said exit leading to said measuring chamber.

6. The cartridge of claim 2, wherein said flow directing chamber further comprises a vent at a gravitationally high location in said chamber.

7. The cartridge of claim 1, wherein said waste means comprises:
(1) a waste chamber, comprising a second vented internal chamber in said housing, and
(2) waste flow means for delivering sample and diluent from said flow directing chamber to said waste chamber by capillary and gravitational forces.

8. The cartridge of claim 1, wherein said waste means comprises a wicking element.

9. The cartridge of claim 1, wherein said sample receiving means is an external chamber on a surface of said housing, said diluent receiving means is (1) an external chamber on a surface of said housing or (2) a third vented internal chamber in said housing, and said diluent receiving means is located at a height below the sample receiving means.

10. The cartridge of claim 9, wherein said diluent receiving means comprises said third vented internal chamber containing a diluent in a sealed container.

11. The cartridge of claim 10, wherein said diluent receiving means chamber has an upper surface, said sample receiving means comprises a chamber open to the external environment and having an upper lip, said upper surface of said diluent receiving means chamber being lower than said upper lip of said sample receiving means.

12. The cartridge of claim 1, wherein said housing further comprises a mixture isolating chamber hydrostatically connected to the receiving chamber, whereby a representative sample of a mixture of sample and diluent in said receiving chamber can be isolated in said mixture isolating chamber.

13. The cartridge of claim 12, further comprising valve means selectively preventing flow from the receiving chamber to the mixture isolating chamber.

14. The cartridge of claim 13, wherein said valve comprises a resilient blocking member capable of obstructing said mixture flow means.

15. The cartridge of claim 14, wherein said blocking member is biased to allow flow through said mixture flow means in the absence of externally applied forces on said blocking member.

16. The cartridge of claim 14, wherein said valve further comprises an access port sealed with a resilient seal through which an external force can be applied to said blocking member to impart motion to said blocking member.

17. The cartridge of claim 12, wherein said mixture isolating chamber comprises:
a valve controlling exit of said mixture form said receiving chamber,
a mixture flow directing chamber, comprising a third internal chamber in said housing,
mixture flow means for delivering mixture from said valve to said mixture flow directing chamber,
second diluent receiving means for receiving a second diluent,
second diluent flow means for delivering said second diluent from said second diluent receiving means to said mixture flow directing chamber,
a mixture receiving chambe, comprising a fourth vented internal chamber in said housing having a third volume,
a mixture measuring chamber, comprising a fourth internal chamber in said housing having a fourth volume smaller than said second volume or said third volume, wherein said mixture measuring chamber connects said mixture flow directing chamber to said mixture receiving chamber and said mixture measuring chamber is capable of delivering mixture and second diluent from said mixture flow directing chamber to said mixture receiving chamber solely by capillary and gravitational forces,
a second stop flow junction located at the intersection of said mixture measuring chamber and said mixture receiving chamber, wherein said second stop flow junction conforms to the surface tension characteristics of said mixture so as to provide sufficient back pressure resulting from contact between said mixture and wall means of said housing at said second stop flow junction to prevent mixture from flowing through said second stop flow junction in absence of second diluent but allowing flow through said stop flow junction when said second diluent receiving means receives second diluent and second diluent enter said mixture flow directing chamber, and mixture waste means for emptying said second flow directing chamber after mixture has entered said mixture flow directing chamber and said mixture has filled said mixture measuring chamber, wherein said waste means operates by capillary and gravitational forces, whereby second diluent added to said second diluent receiving means after mixture has filled said mixture measuring chamber flows through said mixture flow directing chamber and expels mixture from said mixture measuring chamber into said mixture receiving chamber, thereby causing a fixed ratio of mixture to second diluent to be delivered to said mixture receiving chamber.

18. A sample dilution and mixing system, comprising:
the cartridge of claim 17, and
a monitor comprising:
    means for detecting a reaction in the mixture receiving chamber of said cartridge, and
    registration means for holding said cartridge in registration with said detecting means.

19. The system of claim 18, wherein said monitor comprises second system control means adjacent said mixture flow directing chamber when said cartridge is present in said registration means to verify presence of liquid at said second flow directing chamber.

20. The system of claim 19, wherein said second system control means comprises a light source and a detector located on opposite sides of said cartridge when said cartridge is present in said registration means, wherein light emitted by said light source passes through said second flow directing chamber at a light path location and is detected by said detector.

21. The system of claim 20, wherein said light path is located between said mixture measuring chamber exit and said waste means.

22. The system of claim 21, wherein said light path is located to intersect a bottom surface of said second flow directing chamber.

23. The system of claim 18, wherein said monitor comprises third system control means adjacent said mixture measuring chamber when said cartridge is present in said registration means for verifying presence of liquid in said mixture measuring chamber.

24. The system of claim 23, wherein said third system control means comprises a light source and a detector located on opposite sides of said cartridge when said cartridge is present in said registration means, wherein light emitted by said light source passes through said mixture measuring chamber at a light path location and is detected by said detector.

25. The system of claim 24, wherein said light path is located adjacent said second stop flow junction.

26. The system of claim 18, wherein said monitor selects a program by which to operate said valve means by detecting a signal from said cartridge when said cartridge is inserted into said monitor.

27. The system of claim 26, wherein said signal is a bar code.

28. A sample dilution and mixing system, comprising:
the cartridge of claim 1, and
a monitor comprising:
    means for detecting a reaction in the receiving chamber of said cartridge, and
    registration means for holding said cartridge in registration with said detecting means.

29. The system of claim 28, wherein said detecting means comprises a light source and a light detector arranged to detect light passing through said receiving chamber.

30. The system of claim 29, wherein said flow directing chamber comprises:
    exits for said measuring chamber and said waste means at gravitationally low points in said flow directing chamber, and
    entrances for said sample and diluent flow means gravitationally above said exit and said waste means.

31. The system of claim 30, wherein said monitor further comprises system control means adjacent said flow directing chamber when said cartridge is present in said registration means to verify presence of liquid at said flow directing chamber.

32. The system of claim 31, wherein said system control means comprises a light source and a detector located on opposite sides of said cartridge when said cartridge is present in said registration means, wherein light emitted by said light source passes through said flow directing chamber at a light path location and is detected by said detector.

33. The system of claim 32, wherein said light path is located between said measuring chamber exit and said waste means.

34. The system of claim 30, wherein said light path is located to intersect a bottom surface of said flow directing chamber.

35. The system of claim 28, wherein said diluent receiving means in said cartridge comprises a diluent chamber containing said diluent enclosed in a rupturable container and said diluent chamber comprises an access port sealed with a flexible sealing member.

36. The system of claim 35, wherein said monitor comprises programmed diluent control means and said container is ruptured under control of said diluent control means.

37. The system of claim 35, wherein said diluent control means comprises a rupturing pin, said pin being capable of motion into said diluent chamber through said access port under control of said programmed diluent control means without rupturing said flexible sealing member, whereby motion of said pin into said diluent chamber ruptures said container and allows said diluent to enter said diluent flow means.

38. In a dilution and mixing cartridge for automatically diluting a liquid sample with a liquid diluent comprising, in a housing, a sample receiving site, a diluent receiving site, a sample measuring chamber, means for delivering sample and diluent to said sample measuring chamber from said sample receiving site and said diluent receiving site, respectively, a stop flow junction terminating said sample measuring chamber and conforming to the surface tension characteristics of the sample so as to provide sufficient back pressure resulting from contact between said sample and wall means of said housing at said stop flow junction to prevent sample from flowing through said stop flow junction in absence of diluent but allowing flow through said stop flow junction when said diluent receiving means receives diluent, a receiving chamber for receiving a mixture of sample and diluent from said measuring chamber, and means for delivering sample and diluent from said sample measuring chamber to said receiving chamber, the improvement which comprises:

- a flow directing chamber, comprising an internal chamber in said housing, wherein said means for delivering sample to said sample measuring chamber and said means for delivering diluent to said sample measuring chamber both enter said flow directing chamber and an exit in said flow directing chamber leads to said sample measuring chamber; and
- waste means for emptying said flow directing chamber after sample has entered said flow directing chamber and said sample has filled said measuring chamber, said waste means being located in said flow directing means and operating by capillary and gravitational forces.

39. In a dilution and mixing cartridge for automatically diluting a liquid sample with a liquid diluent comprising a sample receiving site, a diluent receiving site, a sample measuring chamber, means for delivering sample and diluent to said sample measuring chamber from said sample receiving site and said diluent receiving site, respectively, a stop flow junction terminating said sample measuring chamber and conforming to the surface tension characteristics of the sample so as to provide sufficient back pressure resulting from contact between said sample and wall means of said housing at said stop flow junction to prevent sample from flowing through said stop flow junction in absence of diluent but allowing flow through said stop flow junction when said diluent receiving means receives diluent, a receiving chamber for receiving a mixture of sample and diluent from said measuring chamber, and means for delivering sample and diluent from said sample measuring chamber to said receiving chamber, the improvement which comprises:

- locating said diluent receiving means gravitationally below said sample receiving means and providing means for preventing hydrostatic pressure from developing between said sample receiving means and said stop flow junction in the absence of diluent.

40. The cartridge of claim 39, wherein said means for preventing hydrostatic pressure is a vented, non-capillary chamber located between said sample receiving means and said stop flow junction.

41. A method for diluting a liquid sample with a liquid diluent, comprising:

sequentially supplying an unmeasured volume of said sample and a measured or unmeasured volume of said diluent to a liquid flow directing chamber, wherein (1) a first portion of said sample entering said flow directing chamber is diverted to a measuring chamber having a first volume, flow of sample through said measuring chamber terminating when said sample reaches a stop flow junction, said stop flow junction conforming to the surface tension characteristics of said sample so as to provide sufficient back pressure resulting from contact between said sample and wall means of said housing at said stop flow junction to prevent sample from flowing through said stop flow junction, the remainder of said sample being diverted by said flow directing chamber to a waste chamber, and (2) a first portion of said diluent entering said flow directing chamber is diverted to said measuring chamber, wherein hydrostatic pressure from said diluent expels said sample in said measuring chamber into a receiving chamber along with said first portion of said diluent, whereby a fixed ratio of sample to diluent is delivered to said receiving chamber.

42. The method of claim 41, further comprising the step of opening first valve means selectively controlling passage of said mixture from said receiving chamber to a hydrostatically connected mixture isolating chamber, wherein a hydrostatically determined portion of said first mixture enters said mixture isolating chamber.

43. The method of claim 42, wherein said device further comprises a second receiving chamber in fluid receiving relationship to said mixture isolating chamber.

44. The method of claim 43, wherein a second diluent is added to said device, wherein said second diluent expels a portion of said mixture in said mixture isolating chamber into said second receiving chamber along with a portion of said diluent, whereby a fixed ratio of said mixture and said second diluent are delivered by capillary and gravitational forces to said second receiving chamber.

* * * * *